United States Patent [19]

Ding et al.

[11] Patent Number: 5,058,589

[45] Date of Patent: Oct. 22, 1991

[54] ELECTRODE FOR MEASURING BODY CURRENTS

[75] Inventors: Wolfgang Ding, Braunschweig; Werner Arnold, Juechen, both of Fed. Rep. of Germany

[73] Assignee: Arbo Medizin-Technologie GmbH, Braunschweig, Fed. Rep. of Germany

[21] Appl. No.: 841,774

[22] Filed: Mar. 20, 1986

[30] Foreign Application Priority Data

Mar. 20, 1985 [DE] Fed. Rep. of Germany ....... 3509976

[51] Int. Cl.⁵ ................................................. A61B 5/00
[52] U.S. Cl. ...................................... 128/640; 128/798
[58] Field of Search ............... 128/639, 640, 641, 798; 339/75 R

[56] References Cited

U.S. PATENT DOCUMENTS

| Re. 31,454 | 12/1983 | Hymes | 128/641 |
| 1,662,446 | 3/1928 | Wappler | 128/798 |
| 3,624,590 | 11/1971 | Bolduc | 339/75 R |
| 4,155,354 | 5/1979 | Rasmussen | 128/640 |
| 4,273,135 | 6/1981 | Larimore et al. | 128/640 |
| 4,299,231 | 11/1981 | Karmann et al. | 128/639 |
| 4,401,356 | 8/1983 | Bare | 128/639 |
| 4,554,924 | 11/1985 | Engel | 128/640 |
| 4,583,549 | 4/1986 | Manoli | 128/640 |
| 4,679,564 | 7/1987 | Sessions | 128/640 |

FOREIGN PATENT DOCUMENTS 3307896  9/1984  Fed. Rep. of Germany.

Primary Examiner—Lee S. Cohen
Assistant Examiner—John P. Lacyk
Attorney, Agent, or Firm—Foley & Lardner

[57] ABSTRACT

An electrode for measuring body currents, comprising an electrically conductive and adhesive contact layer (1) intended for plating on the skin and a cover layer (2) covering the contact layer (1) and a metallic sensor (9, 9'), which is connected to a transmission cable (5), for receiving and transmitting the currents can be easily handled, enables a stable connection to the connecting cable (5) to be established and is provided with an inexpensive part (1, 2) which can be used only once, if the cover foil (2) has an opening (4, 13) at the edge of the electrode and if a clamp (6) is provided which, through the opening (4, 13), grips the underside of the contact layer (1) with a first cheek (7) and the top with a second cheek (8) and which is provided with the metallic sensor (9, 9') and is connected to the transmission cable (5).

6 Claims, 1 Drawing Sheet

ELECTRODE FOR MEASURING BODY CURRENTS

BACKGROUND OF THE INVENTION

The invention relates to an electrode for measuring body currents, comprising an electrically conductive and adhesive contact layer intended for placing on the skin and a cover layer covering the contact layer and a metallic sensor, which is connected to a transmission cable, for receiving and transmitting the currents.

It is known to equip electrodes with an electrically conductive and adhesive contact layer. Such a contact layer can be formed from a viscoelastic gel which contains Karaya and is described, for example, in German Patent Specification 2,727,396. The advantage of these contact layers consists in the fact that they enter into intimate contact with the skin due to their viscoelastic properties and, therefore, produce a low contact resistance between electrode and skin. At the same time, they act as attachment means since they have adhesive properties.

To transmit the body currents to an analysing instrument, a sensor must be provided which is usually formed by a silver/silver chloride layer. In a known embodiment of such an electrode, an AG/AGCl foil having a thickness of 0.02 mm rests on the contact layer and is connected to a pressure stud which projects through the cover layer and to which the transmission cable is attached. Such electrodes are used as single-use electrodes. Their costs are essentially determined by the silver material needed for the sensor.

SUMMARY OF THE INVENTION

The invention is therefore based on the object of producing an electrode of the type initially mentioned which can be used like a single-use electrode and is inexpensive and easy to handle in use.

According to the invention, this object is achieved by the fact that the cover foil is provided at the edge of the electrode with an opening and a clamp is provided which, through the opening, grips the underside of the contact layer with a first cheek and the top with a second cheek and which is provided with the metallic sensor and is connected to the transmission cable.

According to the invention, the part of the electrode which can only be used once only consists of the contact layer and of the cover layer, the cover layer having an opening at the edge of the contact layer. The contact layer is gripped through the opening in the cover layer with the aid of the clamp, the metallic sensor being provided at the clamp.

The opening in the cover layer can be produced, for example, by the contact layer being provided with a lug with is not covered by the cover layer. The clamp is applied to this lug which can be slightly raised as compared with the remaining part of the contact layer.

To obtain accurately reproducible results and a reproducible contacting action, it is advantageous if the second cheek, gripping the top of the contact layer, of the clamp, is provided with a conical pin, if the contact layer is provided with a hole for accommodating the conical pin and if the other cheek of the clamp is provided with a level support face for the contact layer. The sensor can be preferably disposed in the level support face. To increase the contact pressure, it is advantageous if the sensor is disposed to be raised as compared with its surrounding area, which increases the pressure on the contact layer generated by the sensor.

The conical pin moves into the hole in the contact layer to the extent allowed by the size of the hole due to the conicity of the pin. This ensures that the second cheek with the pin produces a distinct annular contact with the contact layer.

In a particularly preferred embodiment, the cover layer is dimensionally stable and preformed in such a manner that it raises the contact layer in the area of the opening in the cover foil. In this arrangement, the end for the clamp is held at a distance from the skin surface so that the clamp can be applied without further manipulations to the electrode bonded to the skin.

BRIEF DESCRIPTION OF THE DRAWINGS

In the text which follows, the invention is to be explained in greater detail with the aid of illustrative embodiments shown in the drawing, in which.

DETAILED DESCRIPTION OF THE PREFERRED EMBODIMENT

Figure 1:
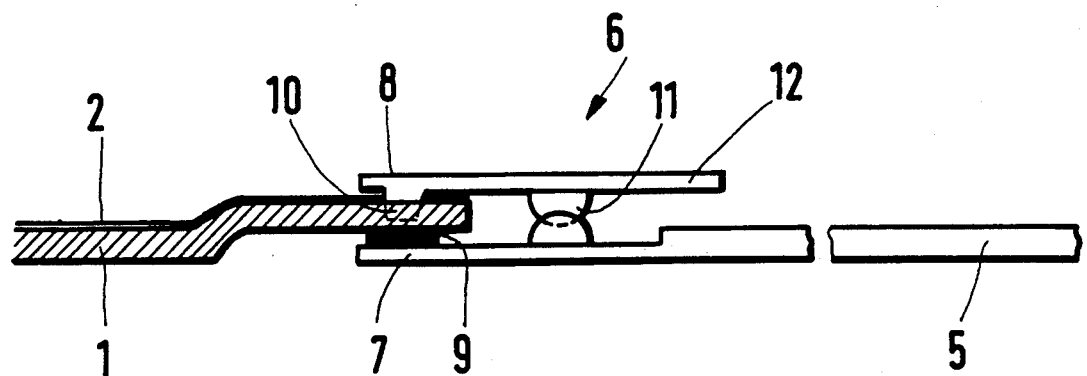
FIG. 1 shows the edge area of a contact layer which is provided with a cover layer, with a clamp with a sensor applied.
Figure 2:
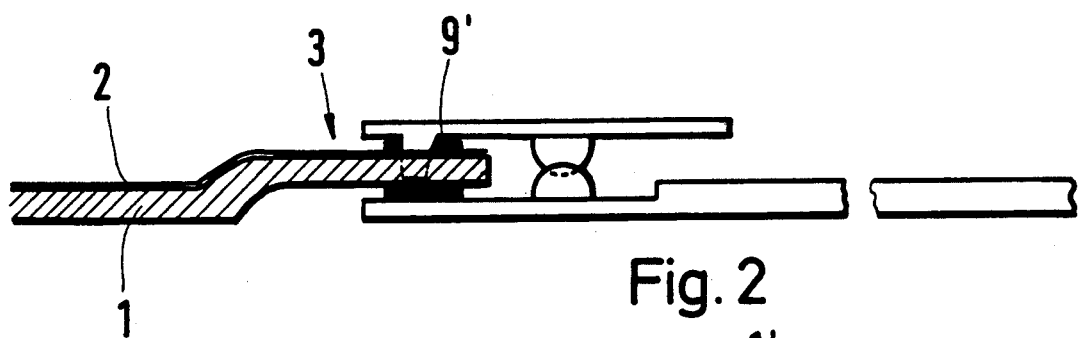
FIG. 2 shows an illustration as in FIG. 1, with a clamp with two sensors.

In FIGS. 1 and 2, the part, which can be used once, of an electrode is formed by a conductive and adhesive contact layer 1 the entire area of which is covered by a cover foil 2. In this arrangement, the cover foil 2 is dimensionally stable and preformed, for example by deep drawing, so that the contact layer is raised at its end, together with the cover foil 2 and extends parallel to the support face. At the raised end 3, the cover layer is provided with an opening in the form of a circular hole which is continued as hole 4 of the contact layer 1. Contact with a connecting cable 5 is established via a clamp 6 which has two cheeks 7, 8 which press against each other elastically. The cheeks 7, 8 of the clamp 6 grip the contact layer 1 in the area of the hole 4, the underside of the contact layer being gripped by the lower first cheek 7 which is provided with a level support face formed by a disk-type sensor 9. In this arrangement, the sensor 9 projects raised over the surrounding area on the inside of the first cheek 7. The contact layer 1 is gripped from the top by the second cheek 8 which is pressed into the hole 4 with a conical pin 10. The largest diameter of the conical pin 10 is significantly larger than the diameter of the hole 4 so that the pin 10 is held by the top edge of the hole 4. The two cheeks are connected to each other at a rotating hinge 11, a lever 12 of the second cheek 8, projecting to the rear past the rotating hinge 11 being used as actuating lever for the clamp 6.

FIG. 2 illustrates that, for securing the contact, the top second cheek 8 can also be provided with a sensor 9' which annularly encloses the conical pin 10 and which presses against the top of the contact layer 1 through a correspondingly expanded opening in the cover foil 2.

Figure 3:
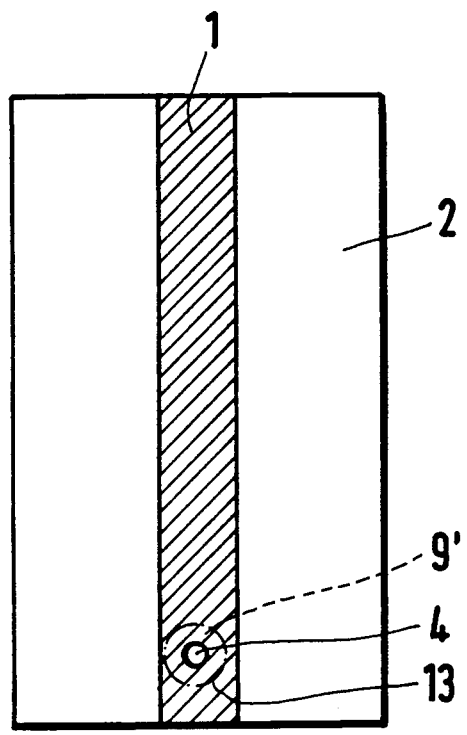
FIG. 3 shows a view from underneath of a strip-shaped contact layer with a cover layer which significantly exceeds the width of the contact layer.

FIG. 3 shows a development of the contact layer 1 and cover foil 2 in which the contact layer is constructed to be strip-shaped and the cover foil has a significantly greater width so that it projects on both sides over the contact layer 1. The underside of the cover foil is, in this case, preferably provided with an adhesive so that the cover foil can support the adhesive effect of the contact layer 1 for pressing the contact layer 1 against the skin.

Figure 4:
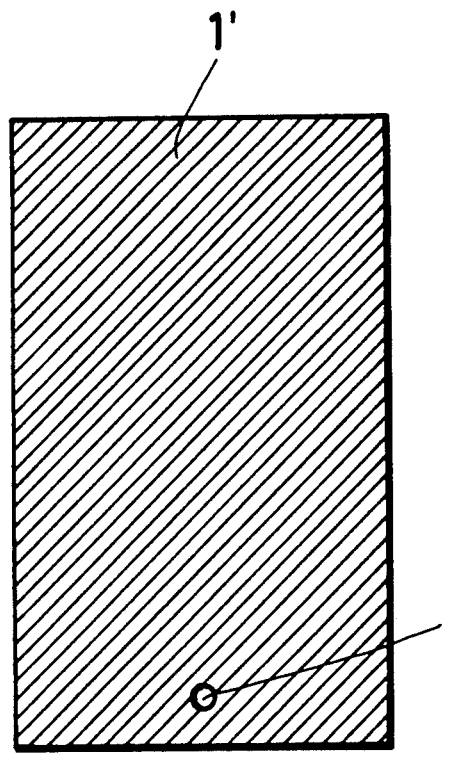
FIG. 4 shows a view from underneath of a contact layer having the size of the cover layer.

In the illustrative embodiment shown in FIG. 4, in contrast, the contact layer 1' takes up the entire area of the cover foil 2 (not shown here) so that the adhesive effect is exclusively caused by the contact layer 1'.

In FIG. 3, the position of the sensor 9' is also indicated for which a correspondingly enlarged opening 13 is provided in the cover foil 2.

What is claimed is:

1. An electrode for measuring body currents, comprising an electrically conductive and adhesive contact layer intended for placement in direct contact on a patient's skin and a preformed and dimensionally stable cover layer covering the contact layer, the cover layer and contact layer being substantially flat along a first portion to be placed in contact with a patient'skin and having a second portion raised above the first portion and a metallic sensor, which is connected to a transmission cable, for receiving and transmitting the currents, wherein an opening is provided at an edge of the cover layer and a clamp is provided which, through the opening, grips the underside of the contact layer with a first cheek and the top with a second cheek and which is provided with the metallic sensor that is connected to the transmission cable.

2. The electrode as claimed in claim 1, wherein the cheek, gripping the top of the contact layer, of the clamp is provided with a conical pin, the contact layer is provided with a hole for accommodating the conical pin, and the other cheek of the clamp is provided with a level support face for the contact layer.

3. The electrode as claimed in claim 2, wherein the level support face is formed by the sensor.

4. The electrode as claimed in claim 1, wherein the sensor is disposed to be raised above the surface of the first and second cheek.

5. An electrode for measuring body currents, said electrode comprising:

(a) an electrically insulating cover layer preformed of a dimensionally stable material having a shape defined by a first portion that is substantially flat and a second portion raised above said first portion, the cover layer having an opening at one edge of the second portion, (b) an electrically conductive and adhesive contact layer bonded to the cover layer and following the shape of the cover layer, (c) a clamp having a first and second cheek, the first and second cheek each having a sensor provided thereon, the clamp being disposed to grip a first surface of the contact layer with the first cheek and a second surface of the contact layer with the second cheek so that the sensors provided on the first and second cheeks make contact with the contact layer, the sensor on the second cheek making contact through the opening in the cover layer, and (d) a transmission cable electrically connected to the sensors.

6. The electrode as claimed in claim 1, wherein the contact layer is provided with an opening that is aligned with the opening in the cover layer, the cheek gripping the second surface being provided with a conical pin that passes through the opening in the contact layer.

* * * * *